US00PP30170P2

(12) United States Plant Patent
Park

(10) Patent No.: US PP30,170 P2
(45) Date of Patent: Jan. 29, 2019

(54) ***GAURA* PLANT NAMED 'URIBLBP'**

(50) Latin Name: *Gaura lindheimeri*
Varietal Denomination: URIBLBP

(71) Applicant: Uriseed Institute, Icheon-si (KR)

(72) Inventor: Kong Young Park, Icheon-si (KR)

(73) Assignee: URISEED INSTITUTE, Icheon-si (KR)

( * ) Notice: Subject to any disclaimer, the term of this patent is extended or adjusted under 35 U.S.C. 154(b) by 11 days.

(21) Appl. No.: 15/530,646

(22) Filed: Feb. 13, 2017

(51) Int. Cl.
*A01H 5/02* (2018.01)

(52) U.S. Cl.
USPC ..... Plt./432

(58) Field of Classification Search
USPC ..... Plt./432
See application file for complete search history.

*Primary Examiner* — Keith O. Robinson
(74) *Attorney, Agent, or Firm* — Penny J. Aguirre

(57) ABSTRACT

A new cultivar of *Gaura lindheimeri*, 'URIBLBP', that is characterized by its flowers that are light pink in color, its abundant number of flower buds per stem, and its compact, dwarf plant habit.

2 Drawing Sheets

Botanical classification: *Gaura lindheimeri.*
Cultivar designation: 'URIBLBP'.

CROSS REFERENCE TO A RELATED APPLICATION

This application is related to a European plant breeders' rights application filed on Sep. 6, 2015, application No. 2015/2072. There have been no offers for sale anywhere in the world prior to the filing of this Application and no accessibility to one of ordinary skill in the art could have been derived from the printed plant breeder's rights documents.

BACKGROUND OF THE INVENTION

The present invention relates to a new and distinct cultivar of *Gaura* plant, botanically of hybrid origin and known as *Gaura lindheimeri* 'URIBLBP' and will be referred to hereinafter by its cultivar name, 'URIBLBP'.

The new invention arose from an ongoing controlled breeding program in Icheon-si, Korea. The objective of the breeding program is to develop cultivars of *Gaura* with unique flower colors and dwarf plant habit.

The new cultivar arose as a mutation using gamma radiation of un-rooted cuttings of *Gaura* 'Baby Butterfly Pearl' (not patented) in 2011. 'URIBLBP' was selected in June of 2011 as a single unique plant.

Asexual propagation of the new cultivar was first accomplished by stem cuttings by the Inventor in Icheon-si, Korea in 2012. Asexual propagation by stem cuttings has determined that the characteristics of the new cultivar are stable and are reproduced true to type in successive generations.

SUMMARY OF THE INVENTION

The following traits have been repeatedly observed and represent the characteristics of 'URIBLBP'. These attributes in combination distinguish 'URIBLBP' as a new and distinct cultivar of *Gaura.*

1. 'URIBLBP' exhibits flowers that are light pink in color.
2. 'URIBLBP' exhibits an abundant number of flower buds per stem.
3. 'URIBLBP' exhibits a compact, dwarf plant habit.

'Baby Butterfly Pearl', the parent plant of 'URIBLBP', differs from 'URIBLBP' in having flowers that are creamy white in color and a taller and less compact plant habit. 'URIBLBP' can be most closely compared to the cultivar 'Passionate Rainbow Petite' (U.S. Plant Pat. No. 23,646). 'Passionate Rainbow Petite' is similar to 'URIBLBP' in having flowers that are pink in color. 'Passionate Rainbow Petite' differs from 'URIBLBP' in having a taller plant height, less flower buds per stem, flowers that are larger and darker pink in color, and foliage that is tricolored.

BRIEF DESCRIPTION OF THE DRAWINGS

The accompanying colored photographs illustrate the overall appearance and distinct characteristics of the new *Gaura*. The photographs were taken of a 6 month-old plant of 'URIBLBP' as grown outdoors in a 13-cm container in Boskoop, The Netherlands.

The photograph in FIG. 1 provides a side view of a plant of 'URIBLBP' in bloom.

Figure 1:
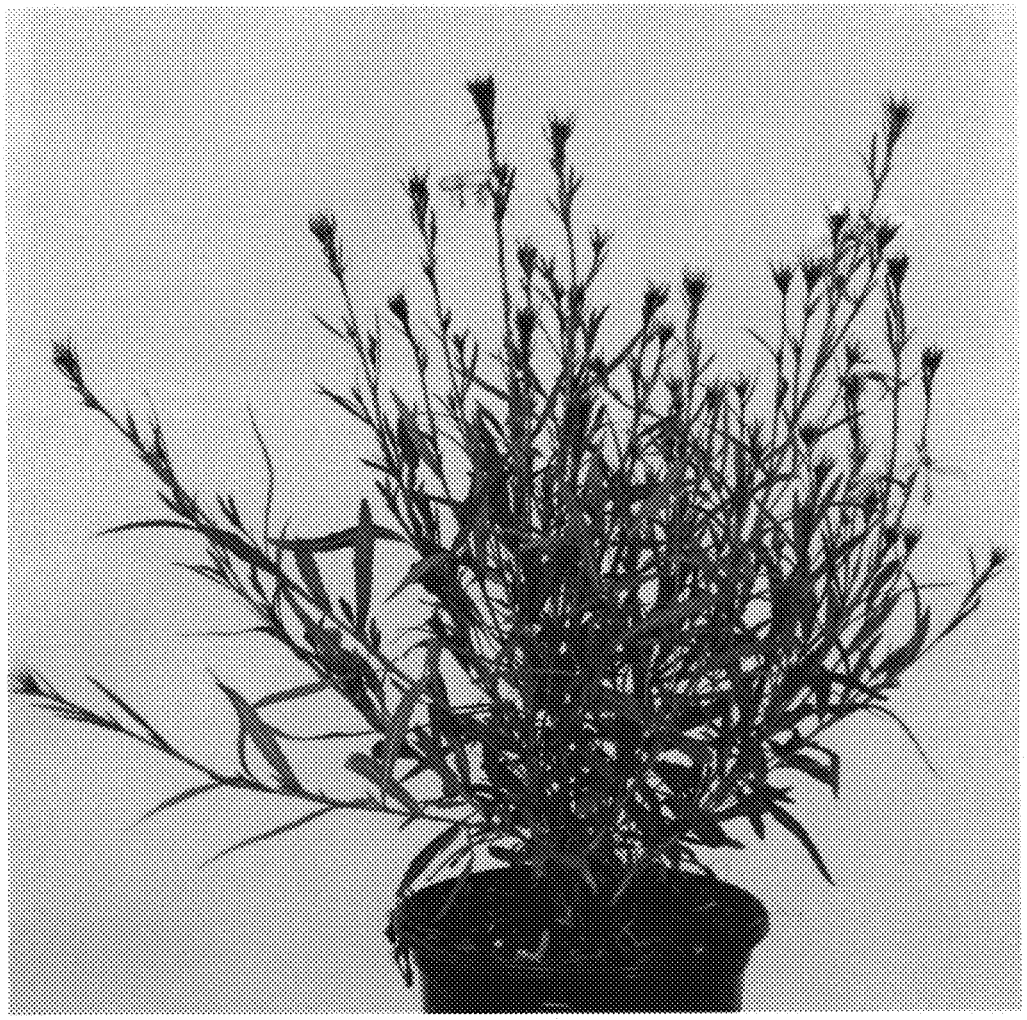
Figure 2:
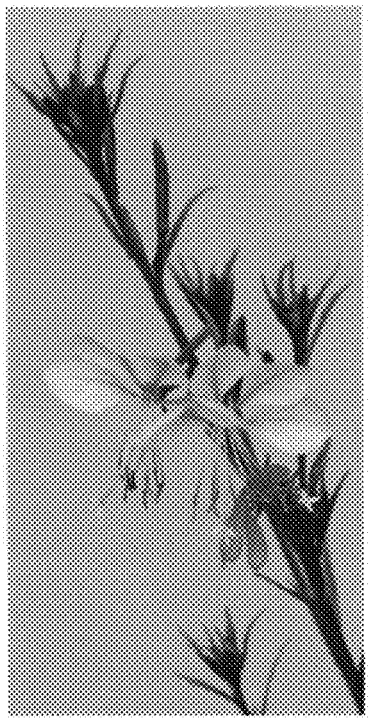

The photograph in FIG. 2 provides a close-up view of the flowers of 'URIBLBP'.

Figure 3:
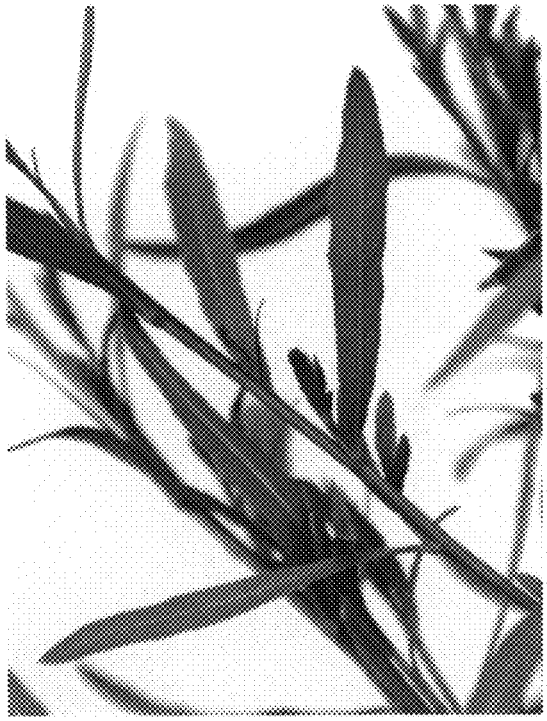

The photograph in FIG. 3 provides a close-up view of the foliage of 'URIBLBP'.

The colors in the photographs may differ slightly from the color values cited in the detailed botanical description, which accurately describe the colors of the new *Gaura.*

DETAILED BOTANICAL DESCRIPTION OF THE PLANT

The following is a detailed description of six month-old plants of the new cultivar as grown outdoors in 13-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—6 weeks in July to September in The Netherlands.

*Plant habit.*—Herbaceous perennial, broad spreading upright.

*Height and spread.*—Reaches about 28.8 cm in height and about 30.1 cm in width.

*Cold hardiness.*—At least to U.S.D.A. Zone 6.

*Diseases and pests.*—No susceptibility or resistance to diseases or pests has been observed.

*Root description.*—Taproot with fibrous secondary roots.

*Branching habit.*—Freely branched, average of 23 branches.

*Growth rate.*—Moderate.

*Propagation.*—Stem cuttings.

*Root development.*—About 25 weeks from a rooted cutting to produce a young plant.

Stem description:

*Stem size.*—Average of 17.5 cm in length and 2 mm in diameter.

*Stem shape.*—Round.

*Stem color.*—137A to 137B, upper side tinged with 187A.

*Stem surface.*—Slightly glossy and sparsely covered with soft hairs average of 0.075 mm in length and 155C in color.

*Stem strength.*—Strong.

*Internode length.*—Average of 9 mm in length.

*Anthocyanin of young shoots.*—Medium (187A).

Foliage description:

*Leaf shape.*—Oblanceolate to narrow elliptic.

*Leaf division.*—Simple.

*Leaf base.*—Long Attenuate.

*Leaf apex.*—Narrowly acute.

*Leaf venation.*—Pinnate, 146C, upper surface; tinged with 176A towards the base, lower surface; 146C, mid rib conspicuousness medium on upper surface and weak on lower surface.

*Leaf margins.*—Shallowly crenate.

*Leaf attachment.*—Petiolate.

*Leaf arrangement.*—Alternate.

*Leaf surface.*—Upper and lower surface glabrous and matte.

*Leaf variegation.*—Absent.

*Leaf color.*—Young upper surface; 146A, mature upper surface; N137D, young lower surface; 146B, mature lower surface; 137B, anthocyanin absent.

*Leaf size.*—Average of 5.1 cm in length and 8 mm in width.

*Petiole.*—Average of 2 mm in length and width, 146C in color.

Flower description:

*Inflorescence type.*—Terminal and axillary racemes.

*Lastingness of flowers.*—Average of 5 days, self cleaning.

*Inflorescence size.*—About 10.8 cm in length and 3.1 cm in width.

*Flower type.*—Single.

*Flower size.*—Average of 3 cm in depth and 2.5 cm in diameter.

*Flower fragrance.*—None.

*Flower number.*—Up to 21 per inflorescence, up to 60 per flowering stem.

*Flower aspect.*—Outward at an average angle of 60° from peduncle.

*Flower bud.*—Narrowly oblong in shape, 1 cm in length, 1.5 mm in width, N186C in color.

*Petals.*—4 per flower, obovate in shape, rotate, smooth, margins entire, about 1.2 cm in length and 6 mm in width, upper and lower surface when opening and fully open 62B in color, veined 67C.

*Sepals.*—4 per flower, linear in shape, strongly reflexed, 1.4 cm in length, 1 mm in width, narrow acute apex, margins entire, upper and lower surface is smooth and moderately glossy, both surfaces color 187C, top 146D.

*Calyx.*—Rotate, strongly reflexed, 1.4 cm in length, 1.1 cm in diameter.

*Peduncle.*—Round, strong, surface is glabrous, an average of 10 cm in length and 1.25 mm in width, held in an angle of 30°, 137B to 137C, tinged 187A in color.

*Pedicel.*—Round, moderately strong, surface is glabrous, an average of 1 cm in length and 1.5 mm in width, held in an angle of 60°, 183A in color.

Reproductive organs:

*Gynoecium.*—1 pistil, 1.9 cm in length, stigma; 4-lobed, 1.75 cm in length, 158D in color, style; 1.75 cm in length, 68B, base 68C in color, ovary; 178A to 178B in color.

*Androecium.*—Stamens; 8, anthers; dorsifixed, narrow oblong in shape, 3 mm in length, 183A in color, filament; 1 cm in length, 68B, base 68C in color, pollen; moderate in abundance and 11D in color.

*Fruit/seed.*—None produced to date.

It is claimed:

1. A new and distinct cultivar of *Gaura* plant named 'URIBLBP' as herein illustrated and described.

* * * * *